US012690763B2

(12) United States Patent
Eom

(10) Patent No.: US 12,690,763 B2
(45) Date of Patent: Jul. 28, 2026

(54) DIAGNOSIS METHOD AND DIAGNOSTIC DEVICE FOR DISTINGUISHING TYPES OF DRY EYE SYNDROME

(71) Applicant: KOREA UNIVERSITY RESEARCH AND BUSINESS FOUNDATION, Seoul (KR)

(72) Inventor: Youngsub Eom, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 996 days.

(21) Appl. No.: 17/788,302

(22) PCT Filed: Dec. 17, 2020

(86) PCT No.: PCT/KR2020/018520
§ 371 (c)(1),
(2) Date: Jun. 23, 2022

(87) PCT Pub. No.: WO2021/132978
PCT Pub. Date: Jul. 1, 2021

(65) Prior Publication Data
US 2023/0025623 A1     Jan. 26, 2023

(30) Foreign Application Priority Data
Dec. 26, 2019     (KR) ........................ 10-2019-0175102

(51) Int. Cl.
*A61B 3/10*          (2006.01)
*A61B 3/00*          (2006.01)
(Continued)

(52) U.S. Cl.
CPC ............ *A61B 3/0025* (2013.01); *A61B 3/101* (2013.01); *A61B 3/14* (2013.01); *A61B 5/015* (2013.01)

(58) Field of Classification Search
CPC .. A61B 6/03; A61B 3/00; A61B 1/043; A61B 3/02; A61B 3/102; A61B 3/1025;
(Continued)

(56) References Cited

U.S. PATENT DOCUMENTS

| | | | |
|---|---|---|---|
| 10,076,250 B2 | 9/2018 | Tzvieli et al. | |
| 2008/0174733 A1* | 7/2008 | Chang ....................... | A61B 3/14 351/206 |

(Continued)

FOREIGN PATENT DOCUMENTS

| | | |
|---|---|---|
| JP | 2008-011983 A | 1/2008 |
| KR | 10-2016-0063174 A | 6/2016 |

(Continued)

OTHER PUBLICATIONS

Wing Li et al., "Ocular Surface Cooling Corresponds to Tear Film Thinning and Breakup", Optometry and Vision Science, Sep. 2015, vol. 92, No. 9, pp. e248-e256.
(Continued)

*Primary Examiner* — Dawayne Pinkney
(74) *Attorney, Agent, or Firm* — Revolution IP, PLLC

(57)          ABSTRACT

A diagnosis method includes: (a) checking tear film break-up time point and location by photographing cornea of the subject's eye and checking in time series at least one or more times of the tear film break-up time point; (b) checking corneal surface temperature by measuring the surface temperature of the cornea of the subject to be evaluated using a thermal imaging camera performed simultaneously with the photographing of the tear film of the eye; (c) mapping the tear film break-up time point and the change in the surface temperature of the cornea based on time; and (d) diagnosing type of dry eye syndrome based on any one of the tear film
(Continued)

break-up time point and a location of surface temperature change time point of the corneal corresponding thereto, in mapping result in step (c).

4 Claims, 6 Drawing Sheets

(51) Int. Cl.

| | |
|---|---|
| *A61B 3/02* | (2006.01) |
| *A61B 3/12* | (2006.01) |
| *A61B 3/14* | (2006.01) |
| *A61B 5/01* | (2006.01) |

(58) Field of Classification Search
CPC ....... A61B 3/113; A61B 3/1015; A61B 3/103; A61B 3/0083; A61B 3/1225; A61B 3/024; A61B 3/005
USPC ................ 351/206, 200, 205, 209–211, 218, 351/221–223, 245–246
See application file for complete search history.

(56) References Cited

U.S. PATENT DOCUMENTS

| | | | | |
|---|---|---|---|---|
| 2012/0057126 | A1* | 3/2012 | Chang | ................... G06T 7/0016 |
| | | | | 351/206 |
| 2013/0079660 | A1* | 3/2013 | Chang | ..................... A61B 5/01 |
| | | | | 600/549 |
| 2019/0254515 | A1 | 8/2019 | Zhang | |
| 2020/0158611 | A1* | 5/2020 | Downie | .............. G01N 33/487 |
| 2020/0383564 | A1* | 12/2020 | Millar | ..................... A61B 3/12 |
| 2021/0068655 | A1* | 3/2021 | Zhang | ................... A61B 3/103 |

FOREIGN PATENT DOCUMENTS

| | | |
|---|---|---|
| KR | 10-1742049 B1 | 6/2017 |
| KR | 10-1776226 B1 | 9/2017 |
| KR | 10-2018-0072911 A | 7/2018 |

OTHER PUBLICATIONS

International Search Report for PCT/KR2020/018520 mailed Apr. 12, 2021 from Korean Intellectual Property Office.

* cited by examiner

[FIG. 1]
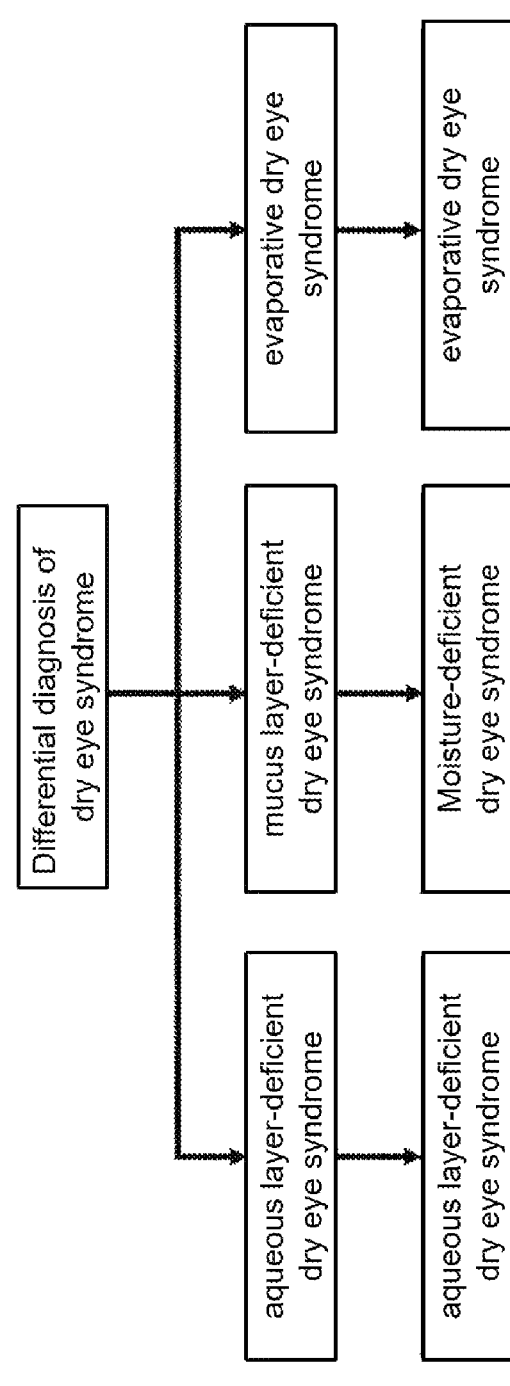

[FIG. 2]

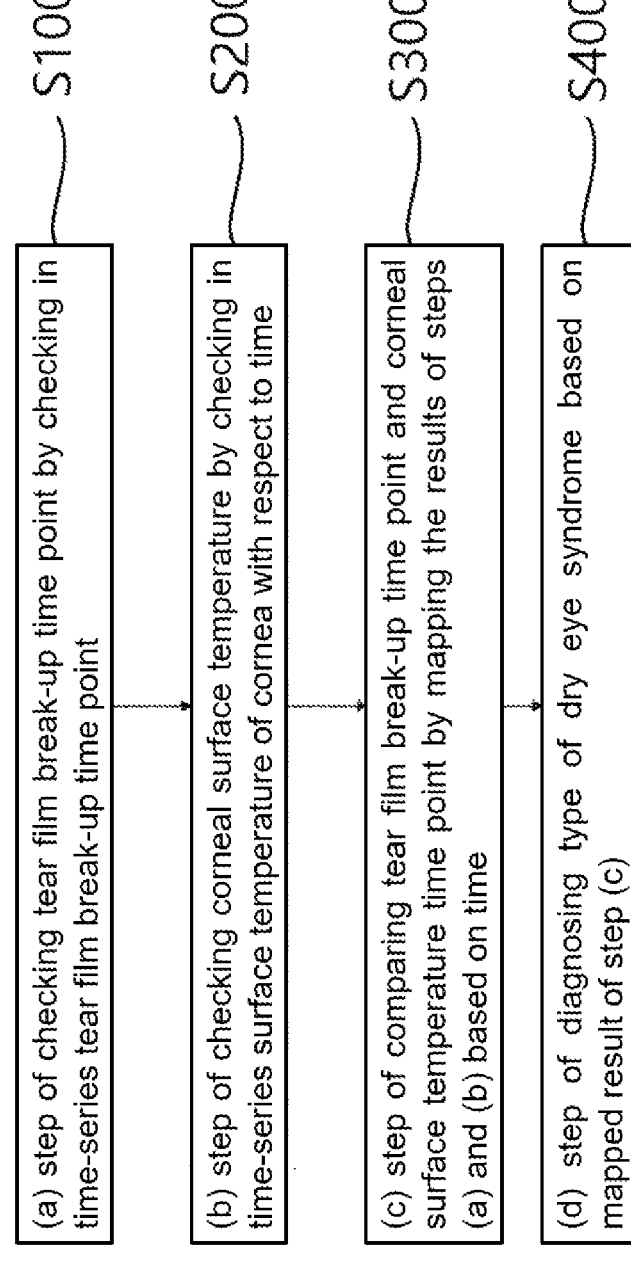

S100

(a) step of checking tear film break-up time point by checking in time-series tear film break-up time point

S200

(b) step of checking corneal surface temperature by checking in time-series surface temperature of cornea with respect to time

S300

(c) step of comparing tear film break-up time point and corneal surface temperature time point by mapping the results of steps (a) and (b) based on time

S400

(d) step of diagnosing type of dry eye syndrome based on mapped result of step (c)

[FIG. 3]
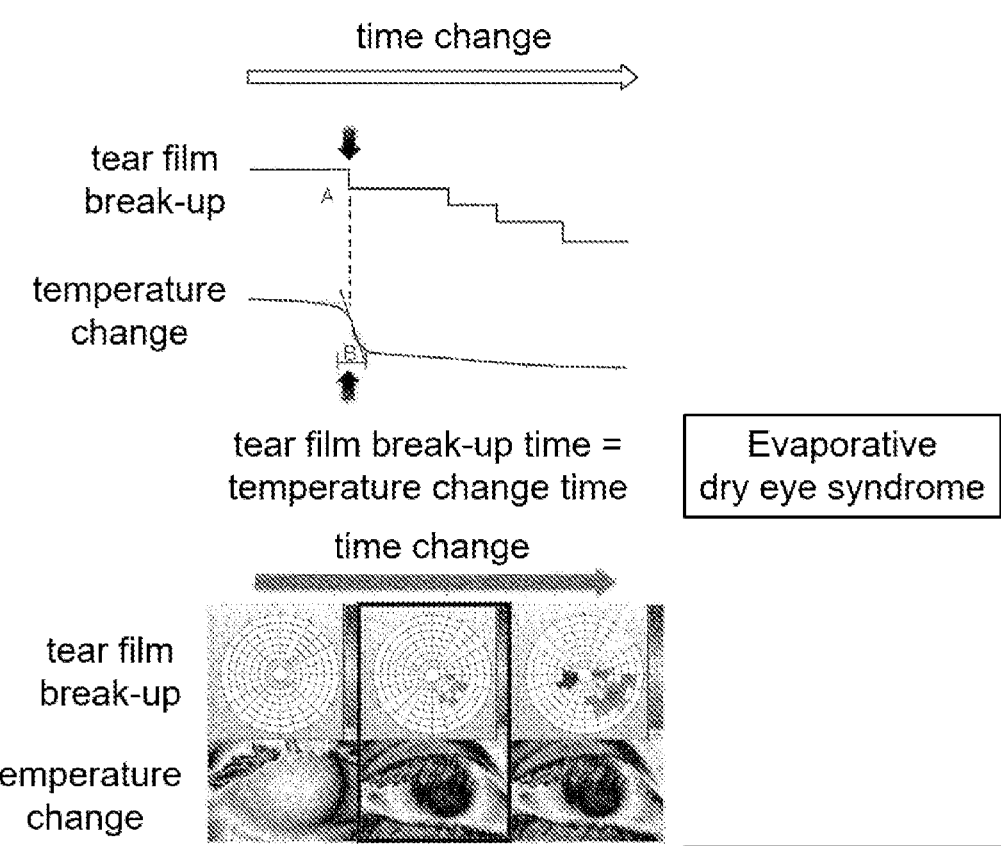

[FIG. 4]
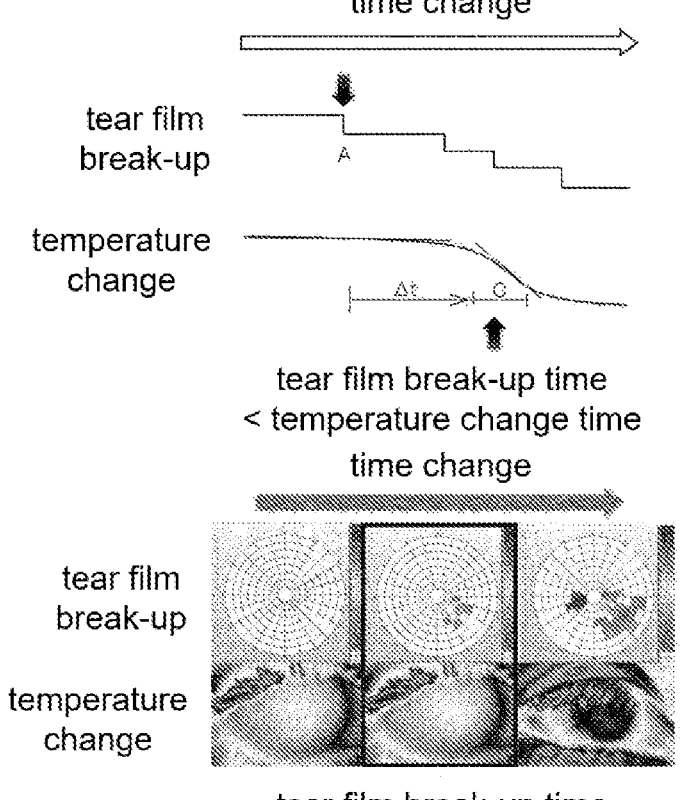
time change
tear film
break-up
temperature
change
tear film break-up time
< temperature change time
mucus layer-
deficient dry eye
syndrome
time change
tear film
break-up
temperature
change
tear film break-up time
< temperature change time
mucus layer-
deficient dry eye
syndrome

[FIG. 5]
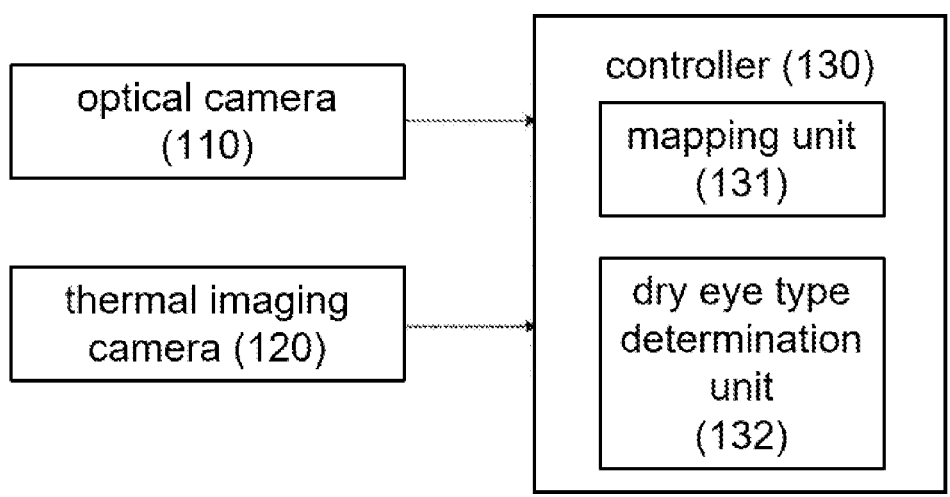

[FIG. 6]
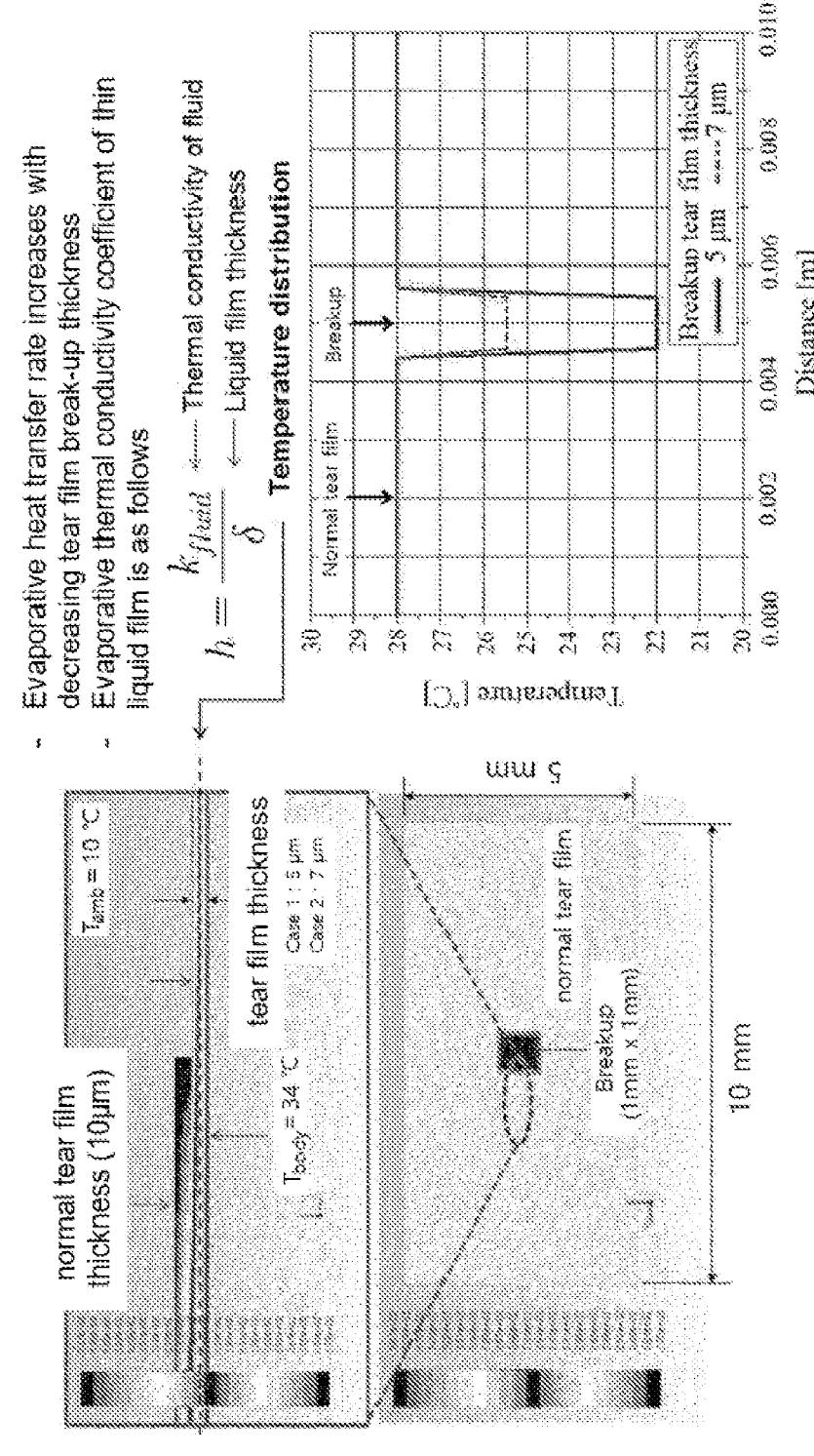

DIAGNOSIS METHOD AND DIAGNOSTIC DEVICE FOR DISTINGUISHING TYPES OF DRY EYE SYNDROME

CROSS REFERENCE TO PRIOR APPLICATIONS

This application is a National Stage Application of PCT International Patent Application No. PCT/KR2020/018520 filed on Dec. 17, 2020, under 35 U.S.C. § 371, which claims priority to Korean Patent Application No. 10-2019-0175102 filed on Dec. 26, 2019 which are all hereby incorporated by reference in their entirety.

TECHNICAL FIELD

The present invention relates to a diagnostic method and a diagnostic apparatus for distinguishing dry eye syndrome types, and more specifically, to a diagnostic method and a diagnostic apparatus for distinguishing dry eye syndrome types in which the type of dry eye syndrome can be identified based on the image reflected from the cornea and the time when the temperature of the corneal surface changes using an optical camera and a thermal imaging camera.

BACKGROUND ART

A dry eye syndrome is an ocular surface disease caused by quantitative/qualitative abnormalities of the tear film. The tear film is composed of three layers, i.e., the mucus layer, the aqueous layer, and the lipid layer. The aqueous layer of the tear film constitutes about 95% of the total tears, and its main role is to supply moisture. The mucus layer constitutes the innermost layer of the tear film, and it allows the aqueous layer to adhere well to the ocular surface and retain moisture. The lipid layer constitutes the outermost layer of the tear film, and since the surface of the aqueous layer is covered with the lipid layer, it stabilizes the air/tear film boundary and prevents the aqueous layer from evaporating.

In case of quantitative/qualitative abnormality in any one of the components of the tear film, namely the mucus layer, the aqueous layer, and the lipid layer occurs, instability of the tear film is induced and dry eye syndrome occurs. Dry eye syndrome can be classified into dry eye syndrome types according to the condition and etiology of the tear layer in which the abnormality occurs. Types of dry eye syndrome include aqueous layer-deficient dry eye syndrome, mucus layer-deficient dry eye syndrome, and lipid layer-deficient dry eye syndrome, as shown in FIG. 1.

Aqueous layer-deficient dry eye syndrome is dry eye disease caused by an insufficient amount of the aqueous layer, which protects the ocular surface and supplies moisture, among the tear film components. Since the aqueous layer accounts for about 95% of the total tears, when the total tear volume is measured and the tear volume is decreased compared to normal, aqueous layer-deficient dry eye syndrome can be diagnosed. Methods for measuring tear volume include the Schirmer Test or similar Strip Meniscometry method to measure tear volume by placing a paper strip or a tip of tube on the edge of the eyelid and on the conjunctiva, and optical coherence tomography (OCT) method to directly measure the height and area of the tear film. Therefore, it is possible to diagnose aqueous layer-deficient dry eye syndrome in actual clinical practice through various diagnostic devices.

Mucus layer-deficient dry eye syndrome is a dry eye syndrome in which the aqueous layer does not adhere well to the ocular surface, especially the corneal surface, due to insufficient mucus layer component in the tear film (decreased wettability), the stability of the tear film is reduced, and the tear film is not evenly distributed on the ocular surface. The mucus layer of the tear film is secreted by goblet cells that exist between the ocular conjunctival epithelial cells. However, since there is no diagnostic device capable of measuring the amount of mucus layer, in actual clinical practice, mucus layer-deficient dry eye syndrome is predicted in an indirect way. To indirectly confirm mucus layer deficiency, based on the mechanism that the tear film stability is lowered and the tear film break-up time is shortened in the case of mucus layer deficiency, the mucous layer deficiency dry eye syndrome is predicted when the tear film beak-up time is shortened by measuring the tear film break-up time. However, there is no way to completely distinguish from mucus layer-deficiency dry eye syndrome because the tear film break-up time is shortened even in lipid layer-deficient dry eye syndrome. In addition, although the mucus layer-deficient can be predicted indirectly by confirming the decrease in goblet cell density measured by conjunctival impression cytology, conjunctival impression cytology is an invasive test method and it is difficult to perform routinely for the differential diagnosis of dry eye syndrome and the actual degree of secretion of the mucous layer cannot be confirmed because it is measured as a decrease in goblet cell density immediately after a decrease in the secretion of the mucous layer, a decrease in the production of the mucous layer, and the hypersecretion of the mucous layer.

Lipid layer-deficient dry eye syndrome is dry eye disease caused by increased evaporation of tears due to the quantitative/qualitative abnormalities of the lipid layer, the outermost layer of the tear film. The lipid layer of the tear film is produced by the meibomian gland on the inside of the eyelid and is supplied to the ocular surface through the meibomian gland outlet at the edge of the eyelid. The increase in tear evaporation can be confirmed by measuring the tear evaporation rate using an evaporator, but there is no clinically commercialized tear evaporation measurement device. Clinically, dry eye syndrome with increased tear evaporation can be diagnosed by confirming the presence or absence of meibomian gland dysfunction, a representative disease that increases tear evaporation, but not all meibomian gland dysfunction is associated with dry eye syndrome. Recently, a diagnostic device for measuring the thickness of the lipid layer has been commercialized and can be used, but the reproducibility of measuring the thickness of the lipid layer is low, and even when the lipid component that does not function normally due to the qualitative change of the lipid component increases, the lipid layer is measured to be thick, and also, there is a limitation in that the thickness of the lipid layer is measured to be thick even when the tear film is contaminated by cosmetics or the amount of the aqueous layer is relatively small and thus the lipid layer is not evenly coated onto the ocular surface.

(Patent Document 1) (Korea Patent Publication No. 10-2018-0072911, Jul. 2, 2018)

DISCLOSURE

Technical Problem

It is an object of the present invention to provide a diagnostic method and a diagnostic apparatus for distinguishing dry eye syndrome types in which the type of dry eye syndrome can be identified based on the image reflected from the cornea and the time when the temperature of the corneal surface changes using an optical camera and a thermal imaging camera.

The object of the present invention is not limited to the object mentioned above, and other objects not mentioned will be clearly understood by those of ordinary skill in the art to which the present invention pertains from the following description.

Technical Solution

In order to achieve the above object, a diagnostic method for distinguishing type of dry eye syndrome according to an embodiment of the present invention comprises (a) checking tear film break-up time point and location by photographing cornea of the subject's eye and checking in time series at least one or more times of the tear film break-up time point, at which the reflected image from the photographed cornea is confirmed to be broken over time; (b) checking corneal surface temperature by measuring the surface temperature of the cornea of the subject to be evaluated using a thermal imaging camera performed simultaneously with the photographing of the tear film of the eye to check in time series a change in the surface temperature of the cornea with respect to time; (c) mapping the tear film break-up time point and the change in the surface temperature of the cornea based on time to compare the tear film break-up time point and time point of the temperature change of the cornea surface; and (d) diagnosing type of dry eye syndrome based on any one of the tear film break-up time point and a location of surface temperature change time point of the corneal corresponding thereto, in mapping result in step (c).

Herein, in step (a), the cornea of the eye may be photographed using an optical camera, and tear film break-up area and location may be calculated based on area and time at which an image is seen to be broken by reflection from the cornea and the time can be confirmed.

Herein, in step (d), if initial tear film break-up time point of the tear film break-up time point corresponds to time point having greatest decrease slope in the temperature change point of the cornea photographed with the thermal imaging camera, it can be determined as evaporative dry eye syndrome, and if the temperature change of the cornea photographed by the thermal imaging camera linearly decreases beyond the time point at which the tear film break-up is observed, and then decreases sharply after a certain period of time so that the temperature change of the cornea is observed later than the initial point of the tear film break-up time point, with respect to the initial point of the tear film break-up time point, it can be determined as mucus layer-deficient dry eye syndrome.

A diagnostic apparatus for distinguishing type of dry eye syndrome according to an embodiment of the present invention comprises an optical camera for taking an image of the eye; a thermal imaging camera for obtaining a thermal image of the eye and measuring temperature change of the eye; and a controller configured to determine the type of dry eye syndrome by mapping and analyzing the image photographed by the optical camera and the thermal image obtained by the thermal imaging camera.

Herein, the controller may comprise a mapping unit for mapping time-series change state of the tear film break-up time point obtained by the optical camera and time-series change state of the surface temperature of the cornea obtained by the thermal imaging camera on a time basis; and dry eye type determination unit for determining the type of dry eye syndrome by comparing initial time point among the tear film break-up time point and the temperature change time point photographed with the thermal imaging camera from two mapped images.

Advantageous Effects

The diagnostic method and diagnostic apparatus for distinguishing type of dry eye syndrome according to the present invention use an optical camera to photograph the cornea of the eye and check in time-series of the tear film break-up time point therefrom, and at the same time, check the surface temperature of the cornea of the subject to be evaluated using a thermal imaging camera and map the two indices based on time, so that the dry eye syndrome type can be more accurately determined based on the location of the tear film break-up time point and the location of the temperature change time point on the corneal surface.

The effects of the present invention are not limited to the above-mentioned effects, and other effects not mentioned will be clearly understood by those of ordinary skill in the art to which the present invention pertains from the following description.

DESCRIPTION OF DRAWINGS

FIG. 1 is a diagram showing the types of dry eye syndrome.

FIG. 2 shows a flowchart of a diagnostic method for distinguishing dry eye syndrome types according to an example of the present invention.

FIG. 3 shows graphs and images of corneal tear film break-up and temperature change for evaporative dry eye syndrome taken through an example of the present invention.

FIG. 4 shows graphs and images of corneal tear film break-up and temperature change for mucus layer-deficient dry eye syndrome taken through an example of the present invention.

FIG. 5 shows a block diagram of an apparatus for diagnosing dry eye syndrome types according to an example of the present invention.

FIG. 6 shows the experimental results related to the heat of evaporation.

BEST MODE

Hereinafter, preferred embodiments of the present invention will be described in detail with reference to the accompanying drawings. In this case, it should be noted that in the accompanying drawings, the same components are denoted by the same reference numerals as much as possible. In addition, detailed descriptions of well-known functions and configurations that may obscure the gist of the present invention will be omitted. For the same reason, some components are exaggerated, omitted, or schematically illustrated in the accompanying drawings.

In addition, throughout the specification, when a part "comprises" a certain component, it means that other components may be further included, rather than excluding other components, unless specifically stated to the contrary. In addition, throughout the specification, "on" means to be located above or below the target part, and does not necessarily mean to be located above the direction of gravity.

Referring to FIG. 2 to FIG. 4, the diagnostic method for distinguishing dry eye syndrome types according to an embodiment of the present invention includes a step of checking tear film break-up time point (S100), a step of checking corneal surface temperature (S200), and a step of comparing tear film break-up time point and the time point of the temperature change of the cornea surface (S300) and a step of diagnosing type of dry eye syndrome (S400).

In the step of checking tear film break-up time point (S100), the cornea of the subject's eye is photographed, and at least one times of the tear film break-up time point, at which the image reflected from the photographed cornea appears to be broken is time-sequentially confirmed. At this time, the cornea of the eye is photographed using an optical camera, and the tear film break-up area and location are calculated based on the area and the time at which the image is seen to be broken by reflection from the cornea, and the time can be confirmed.

The step of checking corneal surface temperature (S200) is performed simultaneously with the photographing of the tear film of the eye, and the surface temperature of the cornea of the subject to be evaluated is checked using a thermal imaging camera to time-sequentially confirm a change in the surface temperature of the cornea with respect to time. In this case, the thermal imaging camera may be disposed adjacent to the optical camera.

In the step of comparing tear film break-up time point and the time point of the temperature change of the cornea surface (S300), the tear film break-up time point and the time point of the surface temperature change of the cornea are compared by mapping the tear film break-up time point and the change in the surface temperature of the cornea based on time.

In the step of diagnosing type of dry eye syndrome (S400), the type of dry eye syndrome is diagnosed based on any one of the tear film break-up time point and the corresponding point of the temperature change of the corneal surface.

At this time, if it is determined that the initial tear film break-up time point (A) of the tear film break-up time point corresponds to time point having greatest decrease slope (B) in the temperature change point of the cornea photographed with the thermal imaging camera, it may be determined as evaporative dry eye syndrome In evaporative dry eye syndrome, when moisture evaporates from the cornea, the surrounding heat of evaporation is absorbed and the temperature decreases. When water evaporates, the absorption of heat of evaporation with time is greatest at the beginning of water evaporation, so the temperature change is measured the most. Therefore, it is possible to predict the timing of the start of tear evaporation by measuring the temperature change of the corneal surface.

If the temperature change of the cornea photographed by the thermal imaging camera linearly decreases beyond the time point at which the tear film break-up is observed (A), and then decreases sharply (C) after a certain period of time (at) so that the sharp temperature change of the cornea is observed later than the initial point of the tear film break-up time point, with respect to the initial point of the tear film break-up time point (A), it is determined as mucus layer-deficient dry eye syndrome. In the case of mucus layer-deficient dry eye syndrome, the tear film is destroyed because the tear film is not properly attached to the corneal surface rather than the evaporation of tears. Therefore, the decrease in temperature due to the absorption of heat of evaporation is less than the evaporative dry eye syndrome, in which the tear film is destroyed by the evaporation of tears, or the temperature decrease occurs after the tear film is destroyed.

Referring to FIG. 5, the diagnostic apparatus for distinguishing dry eye syndrome types according to an embodiment of the present invention includes an optical camera 110, a thermal imaging camera 120, and a controller 130.

The optical camera 110 serves to take an image of the corneal surface.

The thermal imaging camera 120 serves to obtain a thermal image of the corneal surface and to measure (photograph) the temperature change of the corneal surface.

The controller 130 determines the type of dry eye syndrome by mapping and analyzing the image obtained by the optical camera 110 and the thermal image obtained by the thermal imaging camera 120, and a mapping unit 131 and a dry eye type determination unit 132 may be provided.

The mapping unit 131 maps the time-series change state of the tear film break-up time point obtained from the optical camera 110 and the time-series change state of the surface temperature of the cornea obtained from the thermal imaging camera 120 based on time. The dry eye type determination unit 132 determines the type of dry eye syndrome by comparing the initial time point among the tear film break-up time point and the temperature change time point photographed by the thermal imaging camera 120 from the two mapped images.

FIG. 6 shows the experimental results related to the heat of evaporation.

As experimental conditions, the ambient temperature of the corneal surface is 10° C., the inner temperature of the eyeball is 34° C., the thickness of the tear film before the break-up is 10 $\mu$m, the size of the corneal surface is 10 mm×10 mm, and the break-up area is 1 mm×1 mm.

As shown in FIG. 6, it was confirmed that the evaporation heat transfer rate increased as the tear film break-up thickness decreased.

For example, under the surface temperature of the tear layer of the corneal surface of 28° C., it was observed that the corneal surface temperature decreased to 22° C. when the tear evaporation occurred in the tear layer with a thickness of 5 $\mu$m. In addition, it was observed that the corneal surface temperature decreased to 25.5° C. when tears evaporated in the tear layer with a thickness of 7 $\mu$m. In general, the evaporative heat transfer coefficient passing through a thin liquid film may be defined by the equation shown in FIG. 6.

The diagnostic method and diagnostic apparatus for distinguishing type of dry eye syndrome according to the present invention use an optical camera to photograph the cornea of the eye and check in time-series of the tear film break-up time point therefrom, and at the same time, check the surface temperature of the cornea of the subject to be evaluated using a thermal imaging camera and map the two indices based on time, so that the dry eye syndrome type can be more accurately determined based on the location of the tear film break-up time point and the location of the temperature change time point on the corneal surface.

While the present invention has been particularly described with reference to specific embodiments thereof, it is apparent that this specific description is only a preferred embodiment and that the scope of the present invention is not limited thereby to those skilled in the art. It will be apparent to those of ordinary skill in the art to which present invention pertains that other modifications based on the technical spirit of the present invention can be implemented in addition to the embodiments disclosed herein.

The invention claimed is:

1. A diagnostic method for distinguishing a type of dry eye syndrome, comprising:

(a) checking a tear film break-up time point and a break-up location by photographing a cornea of an eye of a subject and checking in time series at least one or more times of the tear film break-up time point, at which a reflected image from the photographed cornea is confirmed to be broken over time;

(b) checking a corneal surface temperature by measuring a surface temperature of the cornea of the subject to be evaluated using a thermal imaging camera performed simultaneously with the photographing of a tear film of the eye to check in time series a change in the surface temperature of the cornea with respect to time;

(c) mapping the tear film break-up time point and the change in the surface temperature of the cornea based on time to compare the tear film break-up time point and a time point of the temperature change of the cornea surface;

(d) diagnosing the type of dry eye syndrome based on any one of the tear film break-up time point and a location of a surface temperature change time point of the cornea corresponding thereto, in a mapping result in step (c), wherein:

the dry eye syndrome is determined to be an evaporative dry eye syndrome, if an initial tear film break-up time point corresponds to a time point having a greatest decrease slope in the temperature change of the cornea; and the dry eye syndrome is determined to be a mucus layer-deficient dry eye syndrome, if the temperature change of the cornea linearly decreases beyond the time point at which the tear film break-up is observed, and then decreases sharply after a certain period of time so that a sharp temperature decrease is observed later than the initial tear film break-up time point; and (e) calculating an evaporative heat transfer coefficient at the break-up location by dividing a thermal conductivity of a tear fluid by a thickness of a tear film at the break-up location, according to a formula $h=k_{fluid}/\delta$, where h is the evaporative heat transfer coefficient, $k_{fluid}$ is the thermal conductivity of the tear fluid, and $\delta$ is the thickness of the tear film at the break-up location, wherein the diagnosing in step (d) is further based on a corneal surface temperature decrease at the break-up location determined from the calculated evaporative heat transfer coefficient, wherein, under conditions of an ambient temperature of the corneal surface of 10° C., an inner temperature of an eyeball of 34° C., a tear film thickness before the break-up of 10 μm, and a surface temperature of a tear layer of the corneal surface of 28° C., the corneal surface temperature decreases to 22° C. when tear evaporation occurs in the tear film having a thickness of 5 μm at the break-up location, and the corneal surface temperature decreases to 25.5° C. when tear evaporation occurs in the tear film having a thickness of 7 μm at the break-up location.

2. The diagnostic method for distinguishing type of dry eye syndrome of claim 1, wherein in step (a), the cornea of the eye is photographed using an optical camera, and tear film break-up area and location are calculated based on area and time at which an image is seen to be broken by reflection from the cornea and the time is confirmed.

3. A diagnostic apparatus for distinguishing a type of dry eye syndrome, comprising:

an optical camera for taking an image of a cornea of an eye;

a thermal imaging camera for obtaining a thermal image of the cornea of the eye and measuring a temperature change of the cornea; and a controller configured to determine the type of dry eye syndrome by mapping and analyzing the image photographed by the optical camera and the thermal image obtained by the thermal imaging camera, wherein:

the controller is configured to:

determine the dry eye syndrome to be an evaporative dry eye syndrome, if an initial tear film break-up time point corresponds to a time point having a greatest decrease slope in the temperature change of the cornea; and determine the dry eye syndrome to be a mucus layer-deficient dry eye syndrome, if the temperature change of the cornea linearly decreases beyond the time point at which the tear film break-up is observed, and then decreases sharply after a certain period of time so that a sharp temperature decrease is observed later than the initial tear film break-up time point, wherein the controller is further configured to calculate an evaporative heat transfer coefficient at a break-up location by dividing a thermal conductivity of a tear fluid by a thickness of a tear film at the break-up location, according to a formula $h=k_{fluid}/\delta$, where h is the evaporative heat transfer coefficient, $k_{fluid}$ is the thermal conductivity of the tear fluid, and $\delta$ is the thickness of the tear film at the break-up location, wherein the controller determines a corneal surface temperature decrease at the break-up location based on the calculated evaporative heat transfer coefficient, wherein, under conditions of an ambient temperature of the corneal surface of 10° C., an inner temperature of an eyeball of 34° C., a tear film thickness before the break-up of 10 μm, and a surface temperature of a tear layer of the corneal surface of 28° C., the corneal surface temperature decreases to 22° C. when tear evaporation occurs in the tear film having a thickness of 5 μm at the break-up location, and the corneal surface temperature decreases to 25.5° C. when tear evaporation occurs in the tear film having a thickness of 7 μm at the break-up location.

4. The diagnostic apparatus for distinguishing type of dry eye syndrome of claim 3, wherein the controller comprises:

a mapping unit for mapping time-series change state of the tear film break-up time point obtained by the optical camera and time-series change state of the surface temperature of the cornea obtained by the thermal imaging camera on a time basis; and dry eye type determination unit for determining the type of dry eye syndrome by comparing initial time point among the tear film break-up time point and the temperature change time point photographed with the thermal imaging camera from two mapped images.

* * * * *